United States Patent [19]

Marshall

[11] Patent Number: 5,211,628
[45] Date of Patent: May 18, 1993

[54] SYRINGE WITH AUTOMATIC RETRACTING NEEDLE

[76] Inventor: John M. Marshall, 2323 Topswood La., South Bend, Ind. 46614

[21] Appl. No.: 767,372

[22] Filed: Sep. 30, 1991

[51] Int. Cl.⁵ .............................................. A61M 5/32
[52] U.S. Cl. .................... 604/110; 604/195; 604/240; 128/919
[58] Field of Search ................ 604/194–196, 604/192, 218, 187, 110, 240, 263; 128/919

[56] References Cited

U.S. PATENT DOCUMENTS

| | | | |
|---|---|---|---|
| 4,838,869 | 6/1989 | Allard | 604/195 |
| 4,874,382 | 10/1989 | Lindemann et al. | 604/195 |
| 4,904,242 | 2/1990 | Kulli | 604/110 |
| 4,955,870 | 9/1990 | Ridderheim et al. | 604/195 |
| 5,017,187 | 5/1991 | Sullivan | 604/110 |
| 5,019,043 | 5/1991 | Segui Pastor | 604/110 |
| 5,019,044 | 5/1991 | Tsao | 604/110 |
| 5,046,508 | 9/1991 | Weissler | 128/763 |
| 5,049,133 | 9/1991 | Villen Pascual | 604/110 |
| 5,064,419 | 11/1991 | Gaarde | 604/195 |
| 5,084,029 | 1/1992 | Tagliaferri et al. | 604/195 |
| 5,088,986 | 2/1992 | Nusbaum | 604/195 |
| 5,092,853 | 3/1992 | Couvertier | 604/195 |
| 5,114,404 | 5/1992 | Paxton et al. | 604/110 |
| 5,114,410 | 5/1992 | Caralt Batlle | 604/195 |
| 5,122,118 | 6/1992 | Haber et al. | 604/110 |
| 5,125,898 | 6/1992 | Kaufhold et al. | 604/110 |
| 5,167,641 | 12/1992 | Schmitz | 604/196 |

FOREIGN PATENT DOCUMENTS 9108788  6/1991  World Int. Prop. O. .......... 604/195

Primary Examiner—C. Fred Rosenbaum
Assistant Examiner—Mark O. Polutta
Attorney, Agent, or Firm—Thomas J. Dodd

[57] ABSTRACT

A syringe which carries a hypodermic needle for administering an injection to a patient. The syringe also includes a body and a plunger with the plunger including a spring-loaded retractor which draws the needle into the plunger immediately after the injection is administered.

3 Claims, 5 Drawing Sheets

SYRINGE WITH AUTOMATIC RETRACTING NEEDLE

FIELD OF INVENTION

This invention relates to syringes, and will have special application to an injection administering syringe which automatically retracts the attached hypodermic needle after an injection is given.

BACKGROUND OF THE INVENTION

Contamination by accidental needle sticks has recently generated a plethora of inventions in the syringe field. With the increased risk of exposure of medical personnel to AIDS contaminated needles, this concern has grown geometrically over the past few years. Some of the "safety" syringes designed to reduce the risk of accidental sticks are seen in U.S. Pat. Nos. 4,650,468; 4,747,830; and 4,752,290. Other designs purporting to reduce contamination risks undoubtedly are being tried and/or developed to meet this growing crisis.

The main drawback to all of the syringes currently available is the need for manual retraction of the plunger by the user in order to effect retraction of the needle into a safe position. Since medical personnel must often administer scores of injections in a given day, only one lapse of cencentration is all that is necessary to expose the user to the risk of a potentially deadly stick.

SUMMARY OF THE INVENTION

The syringe of this invention provides for a mechanism which automatically retracts the needle into the plunger immediately upon completion of the injection. The nurse or other person who administers the injection need do nothing further other than to dispose of the syringe, secure in the knowledge that he or she will not be accidentally stuck by a possibly contaminated needle.

The syringe includes a retractable block positioned inside the hollow syringe tube which secures the needle. A lock is provided to prevent the needle from moving during injection administration. A retractor member is positioned inside the plunger which mates with the block at about the same time the injection is completed. The retractor member releases the lock to allow a biasing member to automatically draw the block and the connected needle into the plunger so that the tip of the needle is no longer exposed and the user is safe from accidental needle stick.

Accordingly, it is an object of this invention to provide for a novel injection syringe which greatly reduces the probability of accidental needle stick.

Another object is to provide a syringe with a retractable needle, and a mechanism which automatically draws the needle into the plunger when the injection is completed.

Another object is to provide a syringe which is cost-efficient to manufacture and which is mechanically sound.

Other objects will become apparent upon a reading of the following description.

BRIEF DESCRIPTION OF THE DRAWINGS

A preferred embodiment has been depicted for illustrative purposes only wherein.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

Figure 1:
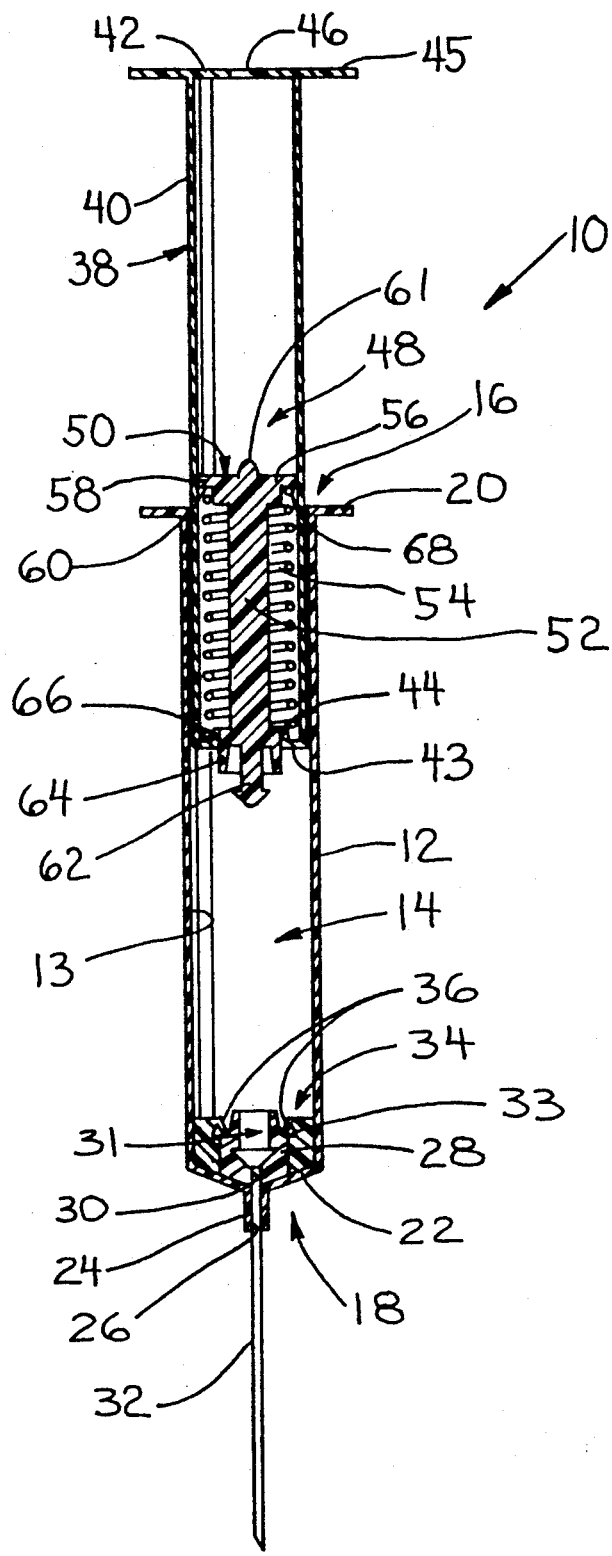
FIG. 1 is a vertical sectional view of the syringe of this invention shown prior to the administration of an injection.
Figure 2:
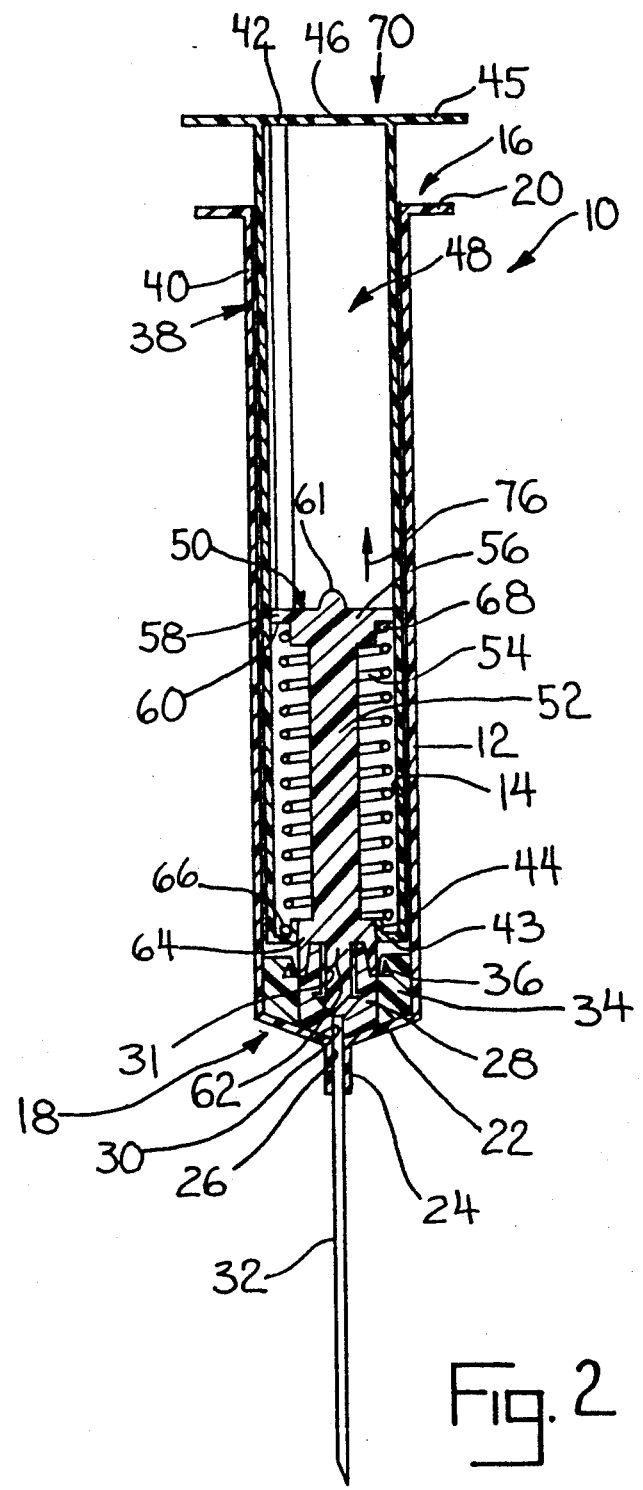
FIG. 2 is a vertical sectional view of the syringe shown at the time the injection is completed.
Figure 3:
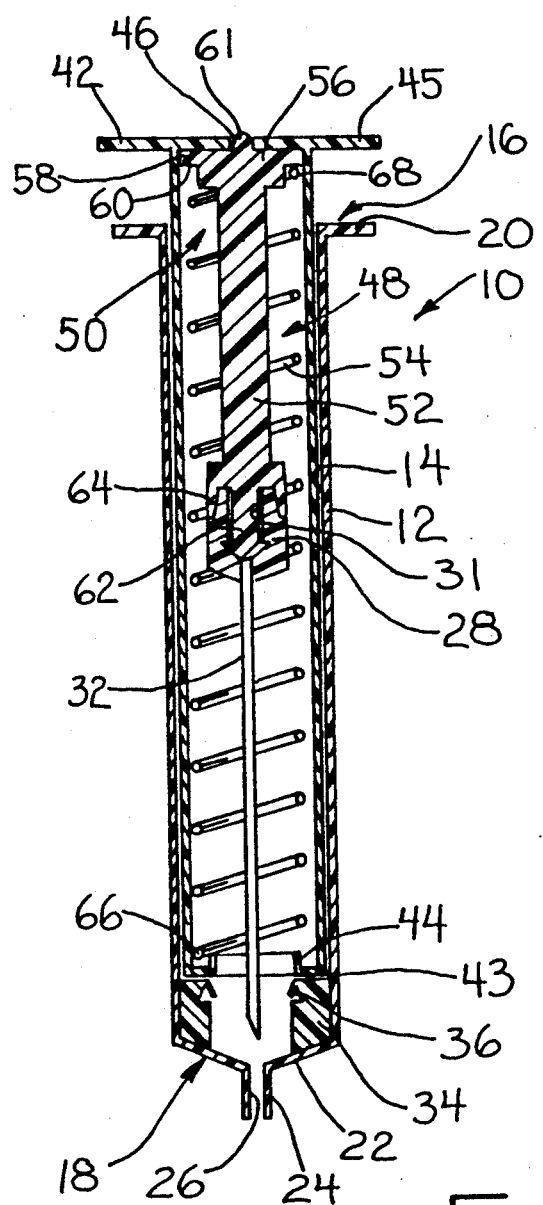
FIG. 3 is a vertical sectional view of the syringe shown immediately following completion of the injection.

Referring first to FIGS. 1-3 reference numeral 10 generally designates the syringe of this invention which is depicted in vertical section view to allow easy identification of its component parts. Syringe 10 includes a hollow tubular member 12 which defines chamber 14 for holding fluids to be injected into the body of a patient. Tubular member 12 as shown includes an upper terminal end 16 and a lower end 18. End 16 defines an outwardly projecting annular ledge 20. Lower end 18 includes a tapered bottom wall 22 which defines annular nipple 24 and injection orifice 26.

Retraction block 28 is positioned in chamber 14 adjacent bottom wall 22. Block 28 has a central opening 30 which is aligned with orifice 26. A conventional hypodermic needle 32 is permanently fastened to block 28 in opening 30 and extends outwardly to tubular member 12. Retraction block 28 is preferably formed from flexible rubber or synthetic material and may have the arrow shaped opening 31 formed therein.

A lock mechanism 34 is also carried within chamber 14 adjacent bottom wall 22. Lock mechanism 34 is also constructed of flexible material and is permanently fixed to tubular member 12 by appropriate means. Lock 34 includes flexible inwardly protruding lip 36 which bears on a shoulder 33 of block 28. This prevents block 28 and its connected needle 32 from being urged into chamber 14 due to pushing forces from the friction encountered as the needle is pushed into the patient.

Plunger 38 is formed of a transparent plastic material and is reciprocably positioned in tubular member 12. Plunger 38 includes outer side wall 40, upper wall 42 and lower wall 43 all integrally molded to form a single piece unit.

Upper wall 42 includes projecting ledge 45 and a central hole 46 as shown. Outer side wall 40 is preferably smooth and fits snugly against the inner portion of side wall 13 of tubular member 12. The smoothness of the walls 13 and 40 allows smooth relative movement of the plunger 38 to provide for irritation-free injections.

Plunger side wall 40 defines an interior plunger chamber 48. A retraction mechanism 50 is positioned in plunger chamber 48 and includes generally a shaft 52 operatively connected to a biasing member which is shown as helical spring 54.

Shaft 52 includes an upper enlarged head 56 which includes uppermost protruding ledge 58 defining shoulder 60. Shaft 52 also includes a lower protrusion 62 which is preferably shaped so as to be matable with opening 31 in block 28. Although protrusion 62 and opening 31 are depicted as arrow shaped in cross-section, any acceptable complemental configurations are possible to achieve the desired result.

Shaft 52 is narrower in diameter than the diameter of plunger side wall 40. Shaft 52 includes an integral annular lower foot part 64 which is firmly press-fitted against upwardly extending lip 44 of plunger lower wall 43. This press-fit allows shaft 52 to remain stationary while the injection is administered and prevents premature retraction of the shaft into the plunger.

Spring 54 circumscribes shaft 52 and has a lower terminal end 66 which bears on plunger lower wall 43 and an upper terminal end 68 which bears against shoulder 60. The compression rating of spring 54 is such that the shaft 52 cannot be retracted into plunger chamber 48 until foot part 64 disengages from its press-fit with lip 44, but is sufficient to draw the block 28 and needle 32 into the plunger chamber when this press-fit is disengaged.

FIG. 1 illustrates syringe 10 with plunger 38 in a pre-injection position. In this position, chamber 14 is filled with a fluid to be injected into a patient (not shown) in a conventional manner.

Figure 5:
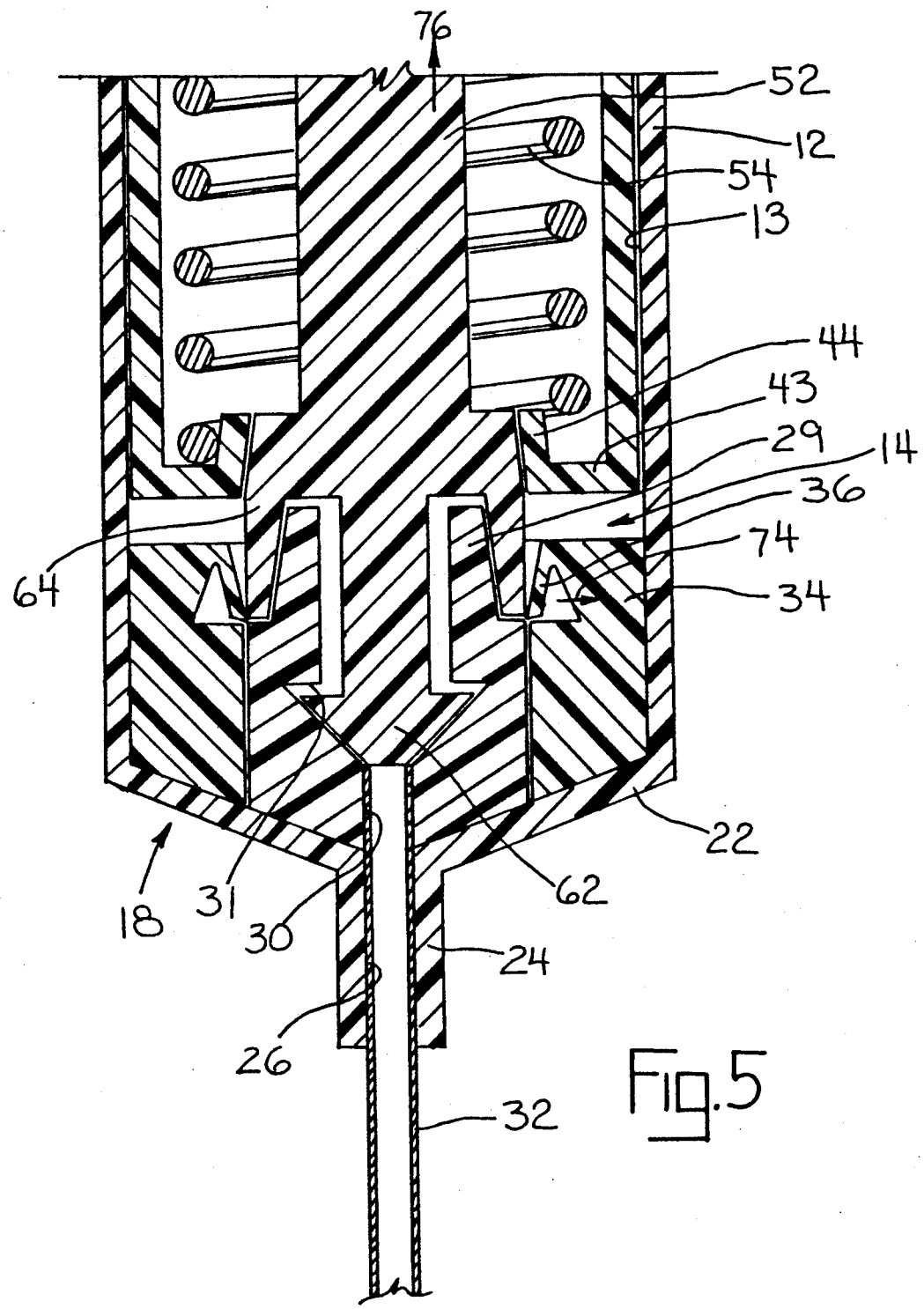
FIG. 5 is a detail sectional view of the block and mechanism at the moment of injection completion.

FIGS. 2 and 5 illustrate the position of plunger 38 at the moment the injection is completed. As the nurse or doctor pushes down on plunger 38 (see arrow 70) fluid is forced through block openings 31 and 30 and through hypodermic needle 32 into the patient's vein (not shown) or under the skin.

Figure 4:
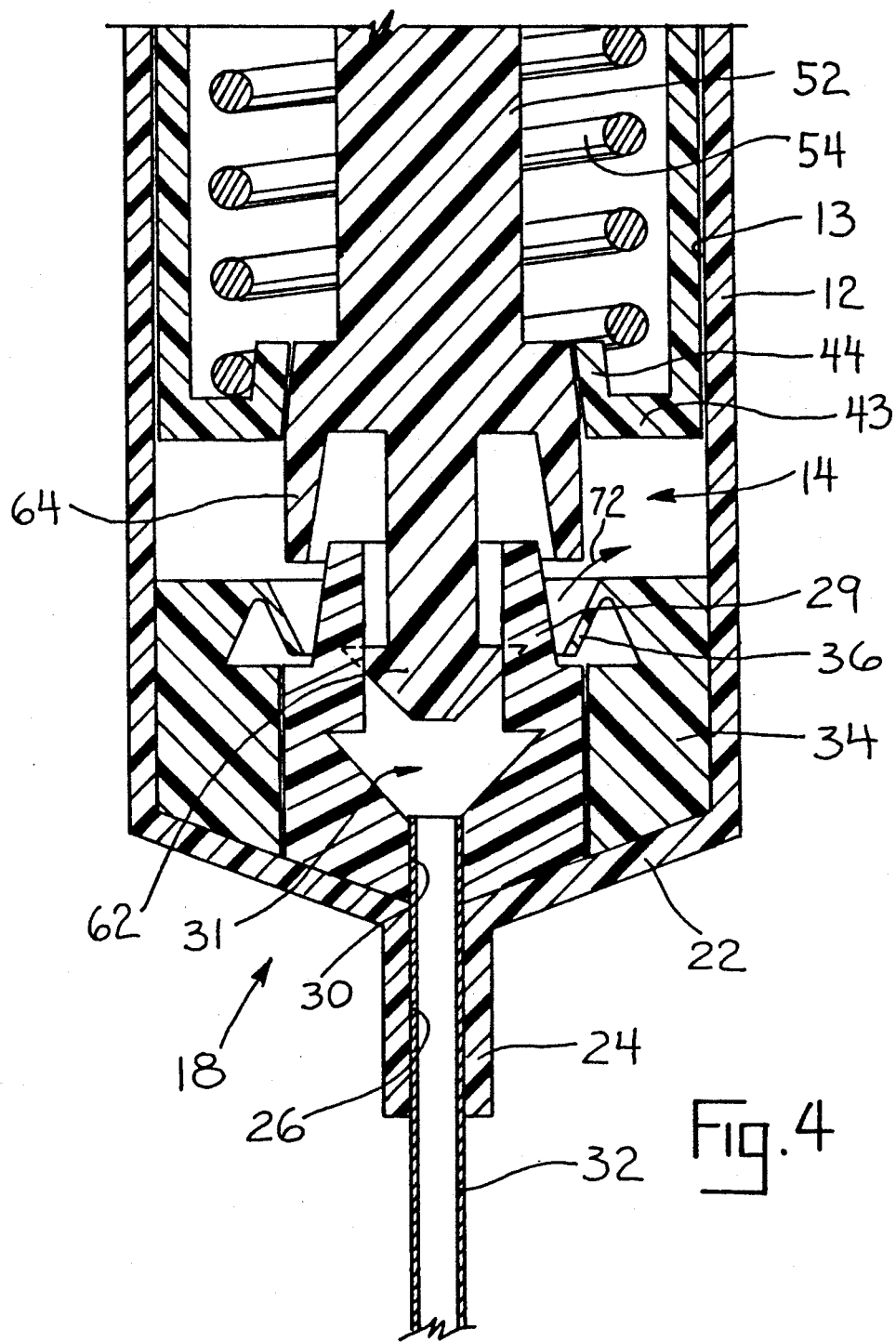
FIG. 4 is a detail sectional view of the retraction block and mechanism as the injection nears completion.

As the plunger 38 is pressed in the direction of arrow 70, protrusion 62 spreads apart the upper annular part 29 of block 28 in the direction of arrow 72 (see FIG. 4) until the protrusion bottoms out in opening 31 (FIG. 5). At this time foot part 64 contacts and spreads lock lip 36 in the direction of arrow 74 to eliminate the force bearing on block shoulder 33.

The residual force of lip 36 against foot part 64 causes a slight inward bend of the foot part inwardly and momentarily causes the foot part to lose contact with plunger lip 44 as shown in FIG. 5. The compressive force of spring 54 then urges shaft head 56 upwardly towards plunger upper wall 42. Due to the mating fit of protrusion 64 in block opening 31, this upward movement is also transferred to block 28 and needle 32 which are urged upwardly (see arrow 76) into plunger chamber 48 as shown in FIG. 5. In this position, which is attained almost immediately upon completion of the injection needle 32 is completely retracted within plunger chamber 48 to prevent accidental needle stick to the injection giver.

As also shown in FIG. 5, the compressive force of spring 54 is preferably sufficiently great so as to urge shaft head 56 into contact with plunger upper wall 42. A nodule 61 of head 56 which may be a different color than plunger 38 is urged into central hole 46 to provide instant visual verification to the user of the needle's retraction. The syringe 10 may then be discarded without fear of accidental needle stick. An additional advantage of the automatic retraction mechanism 50 is the elimination of manual removal of the needle 32 from the patent. Since the needle 32 automatically retracts a split-second after injection completion, the nurse or doctor need not physically pull up on the syringe to remove the needle.

It is understood that the above description does not limit the invention to the given details, but may be modified within the scope of the following claims.

What I claim is:

1. In a syringe for administering injections to a patient, said syringe including a hollow tubular member defining a chamber for storing fluids to be injected, a hypodermic needle connected to a discharge end of said tubular member, and a hollow plunger reciprocally movable between up and down positions in said tubular member, the improvement wherein said needle is fastened to a needle retraction block, lock means fixedly connected to said tubular member within said chamber for securing said block and needle in a first orientation with the needle protruding outwardly of said tubular member, and retraction means carried by said plunger for mating with said block and for disengaging said lock means as the plunger is reciprocated into said full down position, and biasing means located within said plunger and operatively connected to said retraction means, said biasing means for automatically retracting said needle into said plunger when the plunger reaches its full down position, said retraction means includes a shaft which is press-fitted into said plunger, said shaft including a lower protrusion matable with said block for allowing one-way movement of the block, said biasing means includes a spring operatively connected to said shaft within said plunger, said shaft includes a foot part radially spaced from said protrusion, and said lock means includes an inwardly protruding flexible lip bearing on said block, said foot part contacting and bending said lip away from said block when the plunger is in said full down position whereby said lock means is disengaged and flexes the foot inward which removes contact between the plunger and the shaft thus allowing the needle to be retracted.

2. The syringe of claim 1 wherein said shaft includes an upper nodule means for providing a visual indication of needle retraction into said plunger.

3. The syringe in claim 2 wherein said tubular member and said plunger are formed of transparent material.

* * * * *